US00PP22335P2

(12) United States Plant Patent
Pieters

(10) Patent No.: US PP22,335 P2
(45) Date of Patent: Dec. 13, 2011

(54) *CHRYSANTHEMUM* PLANT NAMED 'YELLOW PASSADENA JOGGER'

(50) Latin Name: *Chrysanthemum×morifolium*
Varietal Denomination: Yellow Passadena Jogger

(75) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 0 days.

(21) Appl. No.: 13/066,465

(22) Filed: Apr. 14, 2011

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

| | | | | |
|---|---|---|---|---|
| PP16,233 | P2 * | 2/2006 | Post | Plt./289 |
| PP17,853 | P2 * | 7/2007 | Dekker | Plt./289 |
| PP20,052 | P2 * | 6/2009 | Dekker | Plt./289 |
| PP21,785 | P2 * | 3/2011 | Pieters | Plt./289 |

OTHER PUBLICATIONS

UPOV ROM GTITM Computer Database, GTI Jouve Retrieval Software 2011/01 Citation for 'Yellow Passadena Jogger'.*

* cited by examiner

*Primary Examiner* — Wendy C Haas
(74) *Attorney, Agent, or Firm* — C. A. Whealy

(57) ABSTRACT

A new and distinct cultivar of *Chrysanthemum* plant named 'Yellow Passadena Jogger', characterized by its uniform, upright, outwardly spreading and rounded plant habit; moderately vigorous growth habit; freely branching habit; dense and full plant habit; freely flowering habit; decorative-type inflorescences with bright yellow-colored ray florets; long flowering period; and excellent garden performance.

2 Drawing Sheets

Botanical designation: *Chrysanthemum×morifolium.*

Cultivar denomination: 'YELLOW PASSADENA JOGGER'.

BACKGROUND OF THE INVENTION

The present invention relates to a new and distinct cultivar of *Chrysanthemum* plant, botanically known as *Chrysanthemum×morifolium* and hereinafter referred to by the name 'Yellow Passadena Jogger'.

The new *Chrysanthemum* plant is a naturally-occurring whole plant mutation of *Chrysanthemum×morifolium* 'Passadena Jogger', not patented. The new *Chrysanthemum* plant was discovered and selected by the Inventor as a flowering plant from within a population of plants of 'Passadena Jogger' in a controlled greenhouse environment in Staden-Oostnieuwkerke, Belgium in October, 2008.

Asexual reproduction of the new *Chrysanthemum* plant by vegetative cuttings was first conducted in a controlled greenhouse environment in Staden-Oostnieuwkerke, Belgium in March, 2009. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Yellow Passadena Jogger'. These characteristics in combination distinguish 'Yellow Passadena Jogger' as a new and distinct *Chrysanthemum* plant:

1. Uniform, upright, outwardly spreading and rounded plant habit; moderately vigorous growth habit.
2. Freely branching habit; dense and full plant habit.
3. Freely flowering habit.
4. Decorative-type inflorescences with bright yellow-colored ray florets.
5. Long flowering period.
6. Excellent garden performance.

Plants of the new *Chrysanthemum* differ primarily from the mutation parent, 'Passadena Jogger', in ray floret color as plants of 'Passadena Jogger' have greyed yellow-colored ray florets.

Plants of the new *Chrysanthemum* can also be compared to plants of *Chrysanthemum×morifolium* 'Tardel', not patented. In side-by-side comparisons conducted in Staden-Oostnieuwkerke, Belgium, plants of the new *Chrysanthemum* differed from plants of 'Tardel' in the following characteristics:

1. Plants of the new *Chrysanthemum* flowered earlier than plants of 'Tardel'.
2. Plants of the new *Chrysanthemum* had decorative type inflorescences whereas plants of 'Tardel' had diays type inflorescences.
3. Plants of the new *Chrysanthemum* were not susceptible to Rust pathogens whereas plants of 'Tardel' were susceptible to Rust pathogens.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant. The photograph on the first sheet comprises a side perspective view of a typical flowering plant of 'Yellow Passadena Jogger' grown in a container. The photograph on the second sheet are close-up views of the upper and lower surfaces of typical inflorescences (left) of 'Yellow Passadena Jogger' and upper and lower surfaces of typical leaves (right) of 'Yellow Passadena Jogger'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Yellow Passadena Jogger'.

Parentage: Naturally-occurring whole plant mutation of *Chrysanthemum×morifolium* 'Passadena Jogger', not patented.

Propagation:

*Type.*—Terminal vegetative cuttings.

*Time to initiate roots, summer.*—About 14 days at temperatures of about 20° C.

*Time to initiate roots, winter.*—About 20 days at temperatures of about 20° C.

*Time to produce a rooted young plant, summer.*—About 30 days at temperatures of about 20° C.

*Time to produce a rooted young plant, winter.*—About 40 days at temperatures of about 20° C.

*Root description.*—Fine, fibrous; light brown in color.

*Rooting habit.*—Freely branching; medium density.

Plant description:

*Appearance.*—Perennial *Chrysanthemum* with decorative type inflorescences; stems upright and outwardly spreading giving a uniformly rounded appearance to the plant; very freely branching habit with about 60 lateral branches developing per plant; pinching enhances lateral branch development; dense and full plant habit; moderately vigorous growth habit.

*Plant height.*—About 41.5 cm.

*Plant width.*—About 65 cm.

*Lateral branches.*—Length: About 28.5 cm. Diameter: About 4 mm. Internode length: About 1.9 cm. Strength: Strong. Aspect: Lateral branches positioned about 40° from the main stem. Texture: Densely pubescent; longitudinally ridged. Color: Close to 146C.

*Leaves.*—Arrangement: Alternate, simple. Length: About 3 cm. Width: About 2.3 cm. Shape: Roughly ovate, three-lobed. Apex: Acute. Base: Attenuate. Margin: Palmately lobed and coarsely dentate, sinuses between lateral lobes divergent to parallel. Texture, upper surface: Sparsely pubescent. Texture, lower surface: Densely pubescent. Venation pattern: Pinnate. Color: Developing leaves, upper surface: Close to N137B. Developing leaves, lower surface: Close to 147B. Fully expanded leaves, upper surface: Close to 137B; venation, close to 146C to 146D. Fully expanded leaves, lower surface: Close to 147B; venation, close to 147C. Petiole: Length: About 5 mm. Diameter: About 1.5 mm. Texture, upper and lower surfaces: Densely pubescent. Color, upper surface: Close to 144A. Color, lower surface: Close to 147C to 147D.

Inflorescence description:

*Appearance.*—Decorative inflorescence form; inflorescences borne on terminals above foliar plane; disc and ray florets arranged acropetally on a capitulum.

*Fragrance.*—Moderately fragrant, pungent.

*Flowering response.*—Long flowering period; under natural season conditions, plants flower continuously from mid-September to late October in Belgium.

*Postproduction longevity.*—Inflorescences maintain good color and substance for about three weeks in an outdoor nursery; inflorescences not persistent.

*Quantity of inflorescences.*—About 27 inflorescences develop per lateral branch; about 1,500 inflorescences per plant.

*Inflorescence bud.*—Height: About 7 mm. Diameter: About 6 mm. Shape: Globular. Color: Close to 138B.

*Inflorescence size.*—Diameter: About 2.6 cm. Depth (height): About 1.5 cm. Disc diameter: About 5 mm. Receptacle diameter: About 3.5 mm. Receptacle height: About 2.5 mm. Receptacle color: Close to 145B.

*Ray florets.*—Length: About 1.4 cm. Width: About 4.5 mm. Shape: Narrowly obovate to obovate. Apex: Obtuse to broadly acute. Base: Cuneate. Margin: Entire. Aspect: About 50° from vertical. Texture, upper and lower surfaces: Smooth, glabrous; longitudinally ridged. Number of ray florets per inflorescence: About 70. Color: When opening, upper surface: Close to 5B; at the base, close to 145A to 145B. When opening, lower surface: Close to 5C; at the base, close to 145A to 145B. Fully opened, upper surface: Close to 5B; at the base, close to 145A to 145B; color does not change with development. Fully opened, lower surface: Close to 5C and 6C; at the base, close to 145A to 145B; color does not change with development.

*Disc florets.*—Length: About 7 mm. Diameter: About 1 mm. Shape: Tubular, filiform; apices narrowly acute. Texture, inner and outer surfaces: Smooth, glabrous. Number of disc florets per inflorescence: About 25 massed at the center of the inflorescence. Color, immature: Close to 6C; towards the apex, close to 6B; at the base, close to 145B to 145C. Color, mature: Close to 6C; towards the apex, close to 6B; at the base, close to 145B to 145C.

*Phyllaries.*—Number of phyllaries per inflorescence: About 24 arranged in about three whorls. Length: About 5 mm. Width: About 2 mm. Shape: Ovate. Apex: Bluntly acute. Base: Cuneate. Margin: Entire. Texture, upper surface: Smooth, glabrous. Texture, lower surface: Densely pubescent. Color, upper surface: Close to 147B to 147C; margins, close to N199B. Color, lower surface: Close to 138A; margins, close to N199B.

*Peduncles.*—Length, terminal peduncle: About 4.7 cm. Diameter: About 1.5 mm. Aspect: Erect to about 35° from vertical. Strength: Strong. Texture: Densely pubescent. Color: Close to 138B.

*Reproductive organs.*—Androecium: Not observed. Gynoecium: Present only on ray florets. Quantity: One pistil per floret. Pistil length: About 3 mm. Style length: About 2.5 mm. Style color: Close to 149C. Stigma shape: Cleft, decurrent. Stigma color: Close to 6C.

*Seed/fruit.*—Seed and fruit production have not been observed.

Disease/pest resistance: Plants of the new *Chrysanthemum* have been observed to not be susceptible to Rust pathogens. Resistance to pests and other pathogens common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Yellow Passadena Jogger' as illustrated and described.

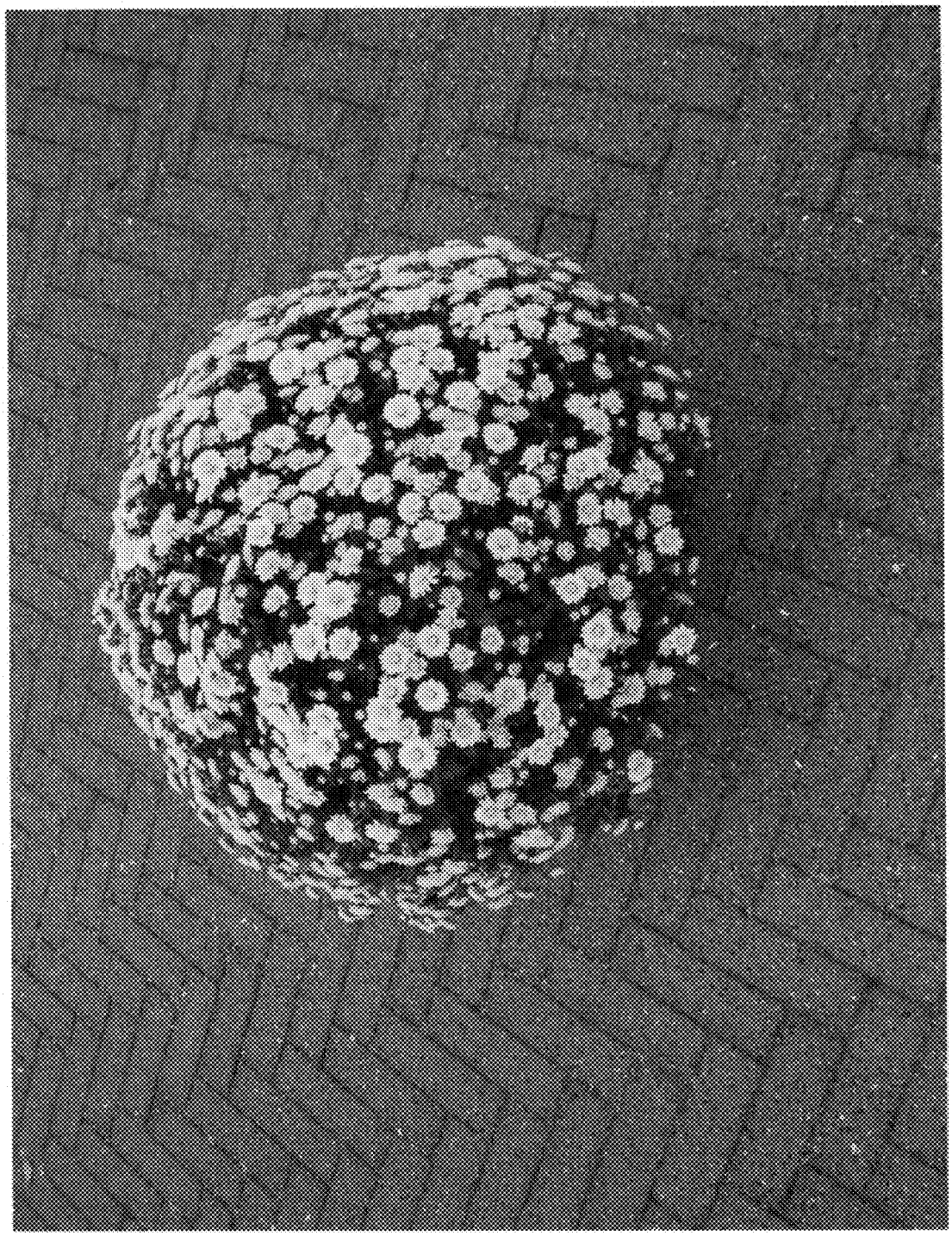

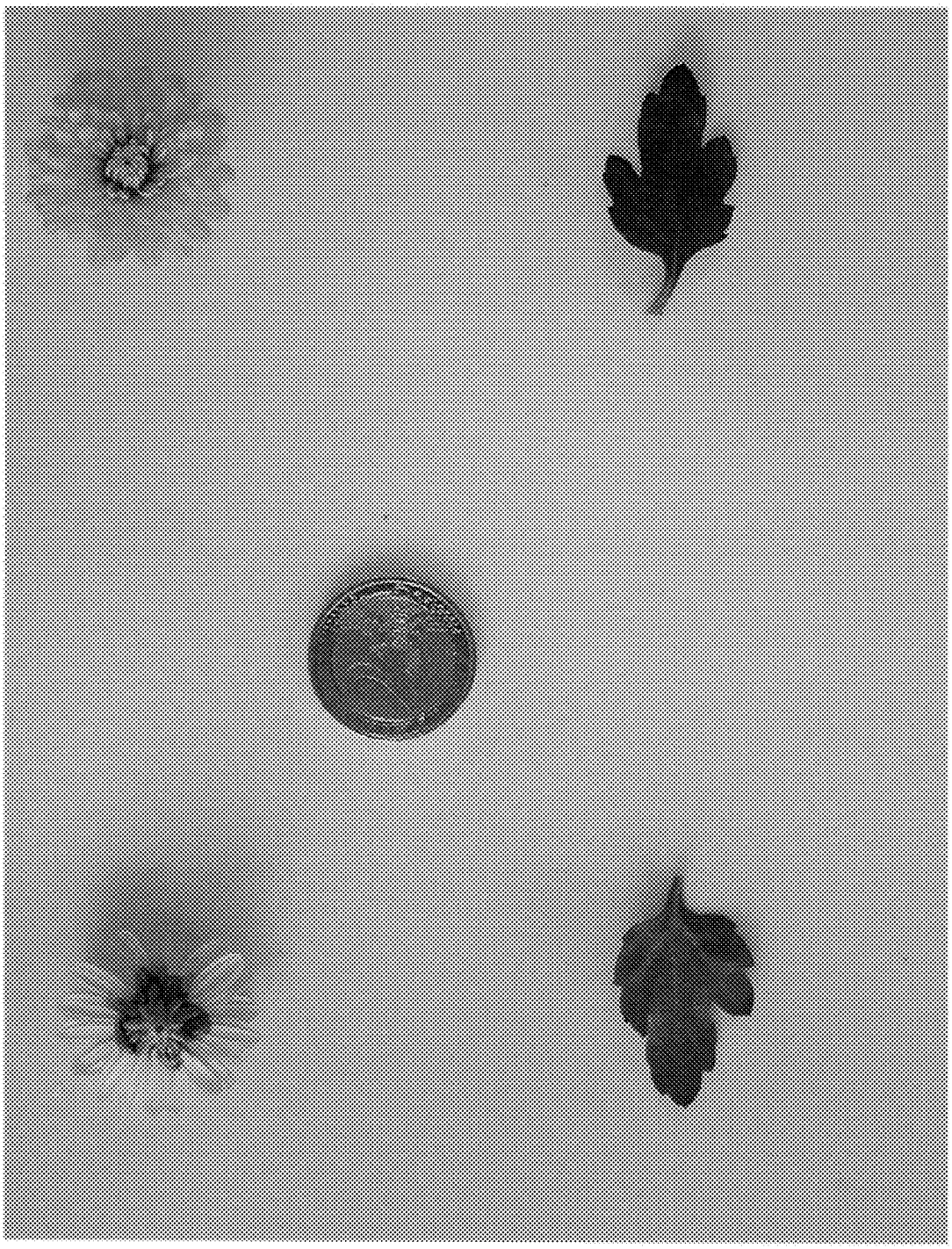

* * * * *